United States Patent [19]
Lal et al.

[11] Patent Number: 5,853,398
[45] Date of Patent: Dec. 29, 1998

[54] CONTAINER WITH PIVOTING TUBE CLAMP

[75] Inventors: Birendra K. Lal, Lake Zurich; Lewis E. Daniels, Jr., Wonder Lake, both of Ill.

[73] Assignee: Baxter International Inc., Deerfield, Ill.

[21] Appl. No.: 994,883

[22] Filed: Dec. 19, 1997

[51] Int. Cl.[6] ................................................ A61M 5/00
[52] U.S. Cl. .......................... 604/250; 604/248; 251/4; 251/9
[58] Field of Search ................................ 604/30, 33, 34, 604/82, 83, 246, 248, 250, 251; 251/4, 9, 10

[56] References Cited

U.S. PATENT DOCUMENTS

| | | |
|---|---|---|
| 2,889,848 | 6/1959 | Redmer . |
| 3,316,935 | 5/1967 | Kaiser et al. . |
| 3,357,674 | 12/1967 | Coanda et al. . |
| 3,374,509 | 3/1968 | Logan et al. . |
| 4,121,622 | 10/1978 | Forberg . |
| 4,248,401 | 2/1981 | Mittleman . |
| 4,307,869 | 12/1981 | Mittleman . |
| 4,434,963 | 3/1984 | Russell . |
| 4,586,691 | 5/1986 | Koslow . |
| 4,932,629 | 6/1990 | Rodomista et al. . |
| 5,401,256 | 3/1995 | Stone et al. . |
| 5,453,098 | 9/1995 | Botts et al. . |

OTHER PUBLICATIONS

Baxter Healthcare Corp.. I.V. Systems Catalog, I.V.Administration Sets p. 51—Buretrol Solution Sets, Published Dec. 1995.

Abbott Laboratories Package Wrap for Nonvented Filter Soluset 150 ×60 with CAIR Clamp; publication date unknown.

Primary Examiner—Ronald Stright, Jr.
Assistant Examiner—Gloria Cavett
Attorney, Agent, or Firm—Jeffrey C. Nichols; Mark J. Buonaiuto; Francis C. Kowalik

[57] ABSTRACT

A flow adjusting tube clamp is used with a chamber in a solution administration device. The tube clamp is pivotally mounted to the cap at a second pivot element. The tube clamp includes first and second elongated tube passages that overly the cap inlet ports as the clamp is pivoted. The tube passages define varying cross-sectional open areas therethrough. The passages are arcuate so that they continuously overly the inlet ports as the clamp is pivoted. The inlet ports are configured to receive flexible tube portions that traverse through the tube passages in the clamp. Each tube passage includes at least one open area and at least one occluding portion to establish and terminate flow therethrough. The clamp is pivotable from a prime position to an intermittent flow position and from an intermittent flow position to a continuous flow position, to effect varying flow conditions.

26 Claims, 3 Drawing Sheets

5,853,398

CONTAINER WITH PIVOTING TUBE CLAMP

FIELD OF THE INVENTION

This invention relates to a multiple flow adjusting tube clamp and chamber for use with a fluid administration device. More particularly, the invention relates to a pivoting multiple flow adjusting tube clamp that is mounted to, and movable about, a chamber in a fluid administration device.

BACKGROUND OF THE INVENTION

Fluid administration devices, such as parenteral administration sets are in widespread use in the medical field. Typically, an administration set includes one or more devices and an interconnecting tubing set. The tubing set and devices may include one or more injection ports for providing, for example, medication such as antibiotics into the fluid path. The set is connected to a fluid supply or source container such as a fluid-filled bag. In one arrangement, the administration set includes a burette chamber which is particularly adapted to contain and provide a known volume of fluid to the patient.

One use for such an administration set is intravenous administration of a solution to a patient. Often, a patient is intravenously fed a steady flow of saline, dextrose or other solution from the supply container. Such administration sets can also be used to provide an added measured amount of a medicament or nutritional elements in a solution to the patient if desired.

In an arrangement to provide a precise amount of fluid to a patent, the solution supply container or bag is connected, in flow communication, with an intermediate burette chamber by a first or upper portion of the administration set. A second or lower portion of the set extends from the burette chamber to the patient. The administration set will typically include one or more clamps, and connectors along the length thereof.

Referring to FIG. 1, a prior art burette chamber 1 is illustrated. The burette chamber 1 holds fluid in an internal chamber 2. A fill tube 3 allows for injecting fluid from a container (not shown) of source fluid or source container into the internal chamber 2, and a vent tube 4 vents the internal chamber 2 to the atmosphere, and the outer end of the vent tube includes a filter 5. A lower administration tube 6 allows for administration from the internal chamber 2 to a patient. Fluid may be injected into the internal chamber 2 through an injection port 7.

A tubing clamp 8 on the fill tube 3 and a tubing clamp 9 on the vent tube 4 are manipulated to adjust the mode of flow of fluid into or out of the internal chamber 2. Users of the burette chamber 1 will likely desire to place the burette chamber; first into either a prime mode; and then select between an intermittent administration or "intermittent" mode; or a continuous mode. In the prime mode, a desired amount of fluid from the source container (not shown) is added to the internal chamber 2. The tubing clamps 8, 9 are manipulated so that both tube 3 and tube 4 respectively are open. A lower tubing clamp 11 is open to prime the rest of the administration tube 6 and regulate the flow. Source fluid flows into the internal chamber 2 and displaced air flows through the vent tube 4 and filter 5. When the desired quantity flows into the internal chamber 2, the clinician decides which mode, intermittent or continuous, they want to operate the device under.

In the intermittent mode, after the burrette chamber has been filled to the desired level as part of the prime mode, clamp 8 is closed and clamp 9 remains open. Air flows through the vent tube 4 into the internal chamber 2 to prevent the drawing of a vacuum in the chamber which may inhibit the flow to the patient. When the desired amount of fluid is administered to the patient, the lower clamp 11 is closed. The process may be repeated as often as desired to give intermittent administration of fluid to the patient.

In the continuous mode, fluid continuously flows through the chamber 2 and onward to the patient. The clamp 8 on the fill tube 3 is opened to provide for the fluid flow from the source container (not shown) into the internal chamber 2 and then out through the administration tube 6. The clamp 9 on the vent tube 4 is closed to prevent the escape of air and a subsequent flooding of the internal chamber 3.

As one can see by the description above, providing for each one of the prime mode, intermittent mode and continues mode requires a unique arrangement of tube clamps 8, and 9 to close or open the corresponding tubing. Remembering these arrangements is troublesome to the provider.

Also, there is nothing to indicate to a user which of the modes the burette chamber 1 is in except for the arrangement of tubing clamps.

Accordingly, there is a need to provide an intermediate chamber which a user can place in various flow modes without requiring the user to remember unique arrangements of individual tubing clamps. A related need is to have a way to indicate to the user when the proper flow mode is achieved.

SUMMARY OF THE INVENTION

A flow regulating tube clamp is used with an intermediate chamber in a parenteral fluid administration device. In an example of a preferred embodiment, the chamber is a burette chamber. The chamber has a main body portion forming an internal chamber and a cap. The cap has at least one and preferably two or more ports and a first pivot element.

The ports are preferably in spaced relation to one another and to the first pivot element. The clamp includes a body portion having a second pivot element engageable with the first pivot element on the cap. Preferably the engagement between the clamp and cap forms a hinge. The body further includes at least one and preferably a plurality of elongated tube receiving passages that are spaced from the second pivoting element. The clamp is configured such that each passage lies at a different radial distance from the second pivot element. Preferably each of these passages are configured as tubing clamps for tubing segments which extend through the passages.

In a preferred embodiment, the first passage defines a varying cross-sectional wide area therethrough such as having outer first and second wide cross-sectional areas connected to one another and contiguous with a narrow, channel-like first occluding portion between the wide areas. Preferably, the first and second wide cross-sectional areas are substantially identical to one another. The clamp is positioned on the cap with the first and second pivot elements engaging one another to form the hinge with the first passage overlying the cap port and a tubing segment extending from the port and passing through the passage.

In an embodiment, the clamp includes a second elongated passage spaced from the first passage, and the chamber cap includes a second port with the second passage overlaying the second port with a tube extending from the second port and passing through the second passage.

In such an embodiment, the second passage includes an elongated wide cross-sectional area contiguous with a second narrow, channel-like occluding portion. In a preferred arrangement, the open area and occluded portion of the first passage correspond to the open portion of the second passage, and the other open portion of the first passage corresponds to the second occluded portion of the second passage. This open-occluded passage arrangement permits the measuring chamber to be set to at least two and preferably three distinct modes of flow, namely, a priming mode, an intermittent mode, and a continuous flow mode.

In a most preferred embodiment, the clamp is mounted to the burette chamber cap and is included within the parenteral administration set. The administration set includes one or more lengths of tubing connecting the chamber to a solution storage container such as an intravenous bag. The burette chamber has the flow adjusting clamp of the subject invention mounted thereto, and a portion of the tubing set extends downward from the chamber to a patient feed device.

In another embodiment, the clamp may include indicia, which when aligned with a marker on a chamber cap, indicate to a user that the clamp is placed in a proper position for a desired flow pattern. Other features and advantages of the present invention will be apparent from the following detailed description, the accompanying drawings, and the appended claims.

DETAILED DESCRIPTION OF THE PREFERRED EMBODIMENTS

Figure 1:
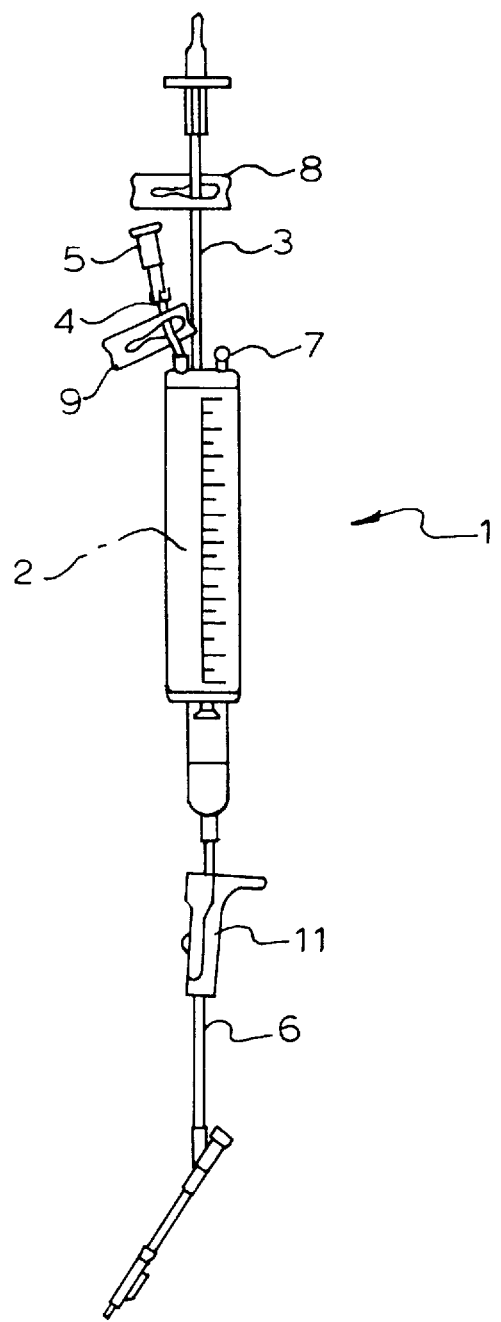
FIG. 1 is a perspective view of a prior art administration set including a solution container spike and a burette chamber having multiple flow adjusting tube clamps and a fitting for connecting the set to a patient feed device.

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiment illustrated.

Figure 2:
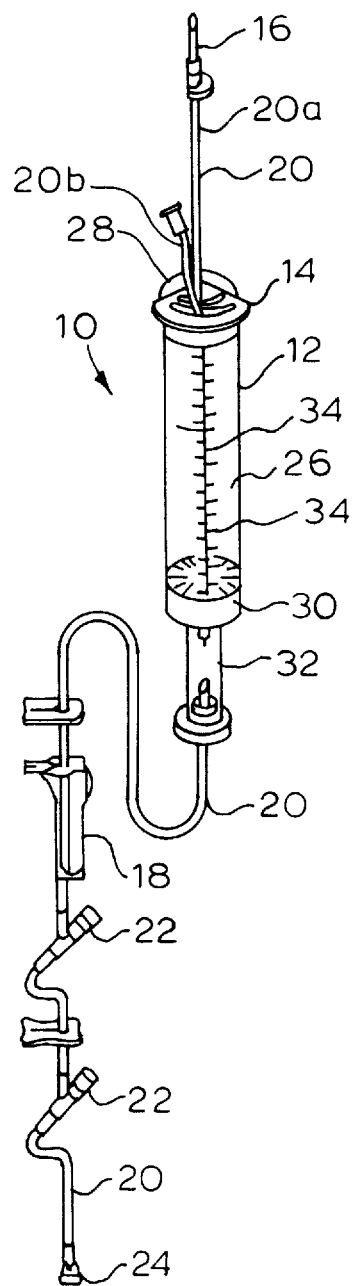
FIG. 2 is a perspective view of an exemplary solution or fluid administration set including a solution container spike and a measuring chamber having a flow adjusting tube clamp in accordance with the principles of the present invention.

Referring now to the figures and in particular to FIG. 2, there is shown a preferred embodiment of a parenteral fluid or solution administration set 10 having a measuring chamber such as a burette chamber 12 including a flow control clamp 14 in accordance with the principles of the present invention. The administration set 10, an example of which is a BURETROL® administration set, available from Baxter International Inc. of Deerfield, Ill., U.S.A., assignee of the present application, is used, typically, for providing a known quantity of a fluid to a patient. The fluid can be provided intravenously, intraperitoneally, or in other ways that will be recognized by those skilled in the art.

In one arrangement, the administration set 10 is connected to a fluid source container (not shown), and includes a spike 16 for connecting the administration set 10 to the container; a measuring chamber 12; various lengths of tubing 20; and one or more injection sites or ports 22. The set 10 also includes a connecting element 24 and a roller clamp 18 to permit connecting the administration set 10 to a patient feed device such as a catheter (not shown). Those skilled in the art will recognize that the particular components and arrangement of components in an administration set 10 can vary widely and that the administration set 10 can include, or be assembled without, certain of the aforementioned components.

Figure 3:
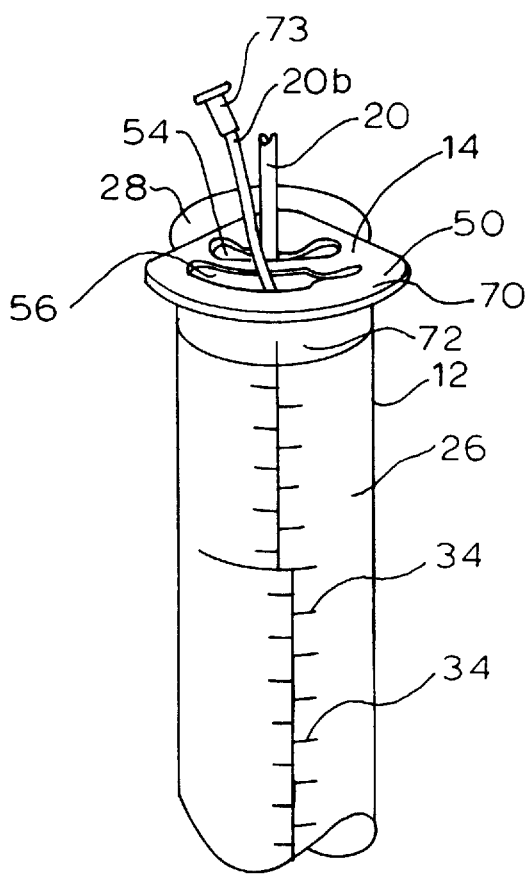
FIG. 3 is an enlarged, partial perspective view of the upper portion of the chamber shown in FIG. 2, illustrating the pivotal flow control clamp of the present invention, in place on the chamber cap.

Referring now to FIGS. 2 and 3, the measuring chamber 12 includes a main body portion 26 and a top cap 28. The chamber 12 can include a bottom cap 30 to which is attached a drip chamber 32. Typically, the chamber body 26 is formed of a transparent material, and will include calibration marks 34 thereon so that the amount of fluid in the chamber 12 can be precisely measured. Thus, the quantity of fluid fed from the chamber 12 to the patient can be controlled.

Figure 4:
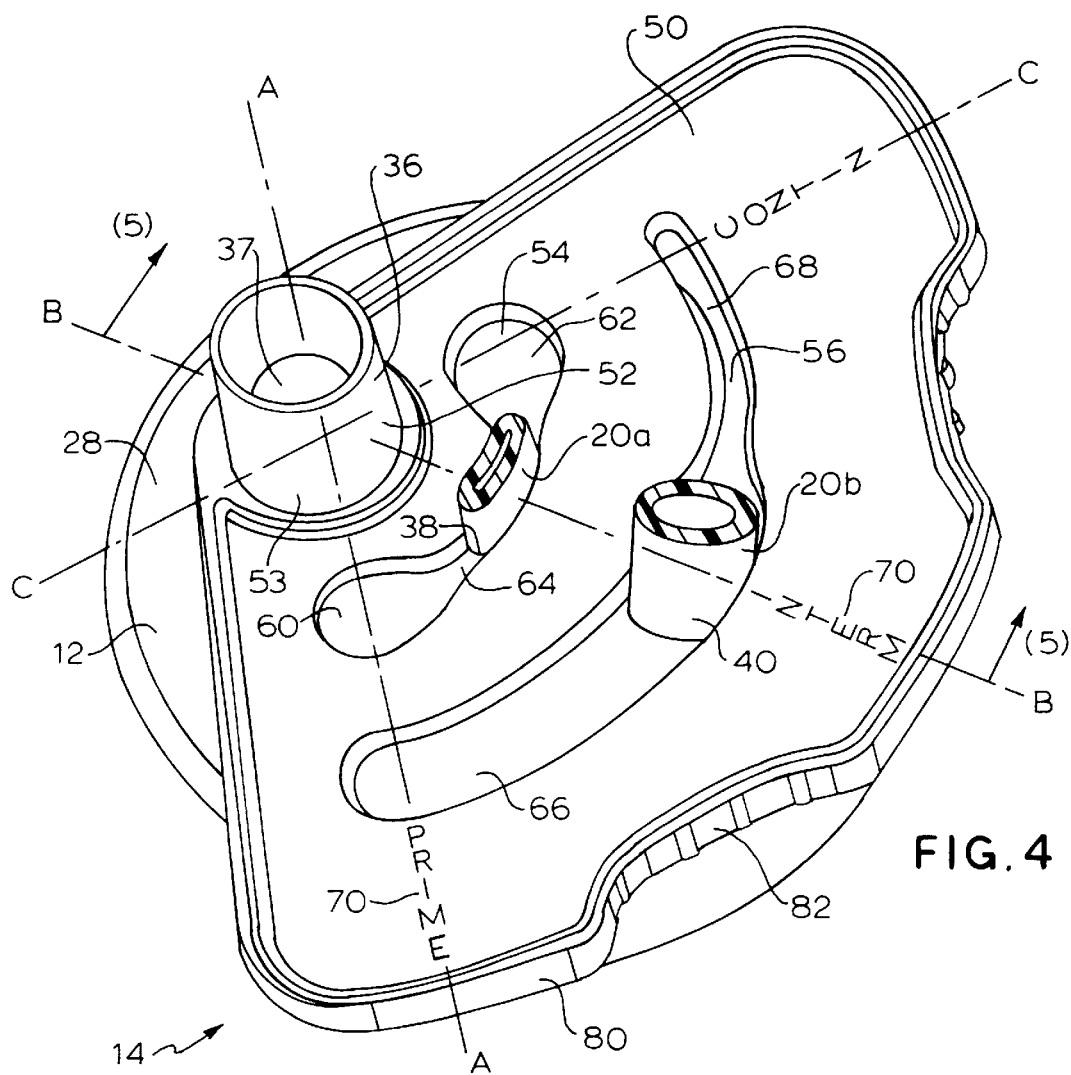
FIG. 4 is a top view of the chamber cap illustrating the flow control clamp of the present invention, illustrated with a tube passing through each of the tube passages.
Figure 5:
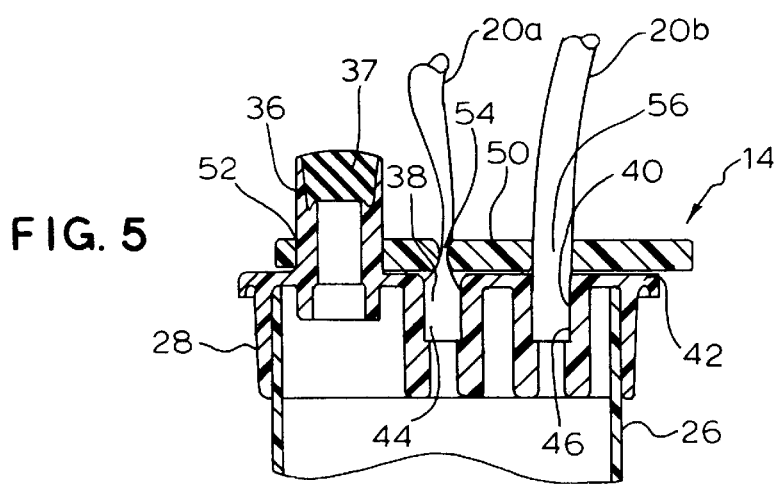
FIG. 5 is a cross-sectional view of the chamber cap and flow control clamp taken along line 5—5 of FIG. 4.

Referring to FIGS. 4 and 5, the top cap 28 includes a first pivot element 36 which is preferably an injection port 37, and at least one, and preferably two, inlet ports 38, 40. As best seen in FIG. 5, the first pivot element 36 is eccentrically positioned on the cap 28. In a preferred embodiment, the inlet ports 38, 40 are formed as openings in the top cap 28. The top cap 28 is fitted into the chamber body 26 and can be secured thereto by methods known in the art.

The first and second inlet ports 38, 40 are in spaced relation relative to one another and relative to the first pivot element 36. The inlet port 38 is connected to flexible tubing 20a such as that used in the administration set 10, and vent port 40 is connected to flexible tubing 20b. The tubings 20a and 20b are received in wells in each the first and second port, 44, 46, respectively, and may be fixedly connected to the inner walls of the wells 44 and 46. The ports 38, 40 provide flow communication between the interior of the chamber 12 and the tubing 20 connected thereto.

The flow control clamp 14 includes a body portion 50 having a second element, for example a passageway 52, that is engagable with the first element 36 on the cap 28 so that the cap 28 is engaged in some manner to the clamp 14 but the clamp 14 is movable relative to the cap 28. Preferably, the clamp 14 is mounted to the cap 28 to form a hinge 53 so as to permit the clamp 14 to pivot about the first element 36 located on the cap 28. The hinge 53 may be provided by a sliding rotational fit between the clamp 14 and an annular recess formed on the injection port 37.

The clamp 14 includes at least one, and preferably a plurality of, such as the exemplary two, elongated flexible tube receiving passages 54, 56 formed therein. The passages 54, 56 correspond to tubings 20a and 20b, respectively, connected to the ports 38 and 40, in the cap 28. The tube passages 54, 56 are in spaced relation relative to one another and to the hinge 53. Preferably the passages are configured as slots.

Preferably, when the clamp 14 is attached to the cap 28 the passages 54, 56 lie at radial distances from the second element 52 so that the first and second passages 54, 56 overlay the cap inlet ports 38, 40. As best seen in FIGS. 4 and 5, the passages 54, 56 have an arcuate shape so that as the clamp 14 is pivoted about the cap 28, the two passages 54, 56 continue to overlay the ports 38, 40.

Referring now to FIG. 4, the tube passages 54, 56 have varying cross-sectional open areas along at least a portion of their length. A preferred first passage 54 has a dog-bone shape including two relatively wide cross-sectional open end areas 60, 62 that taper inwardly toward a relatively narrow, channel-like connecting or occluding portion 64 extending therebetween. Preferably, the open areas 60, 62 are similarly configured. It will be recognized by those skilled in the art, that when a tube segment extends through either of the wide open area end portions 60, 62, the tube 20a will be preferably be unconstricted or unoccluded, and flow therethrough may occur at a relatively high rate. Conversely, when a tube segment extends through the relatively narrow passage 64 connecting the open end areas 60, 62, the tube 20a is pinched in such a manner so that the tube is constricted or occluded and flow therethrough will likewise be reduced to a substantially lower flow rate or stopped.

Pinching is some constriction of the tubing 20a or 20b and ranges from a slight constriction to a total occlusion of the tubing.

A preferred second passage 56 in the clamp 14 includes an elongated wide area portion 66 and a shorter relatively narrow, channel-like constricting or occluding portion 68. The open and occluded portions 66, 68, respectively, function in the same manner as those described above for the first passage 54. That is, when the tube 20b is positioned in the wide open area 66, it is unconstricted and flow therethrough may occur at a relatively higher rate, whereas when the tube 20 is positioned in the constricted area 68, the tube 20 is pinched so that the tube is occluded which, in turn, reduces or stops the flow therethrough.

As seen in FIG. 4, the first and second passages 54, 56 are positioned with their respective wide and narrow portions in predetermined relation to one another. This results in particular, desired flow characteristics in the tubes 20a and 20b when the clamp 14 is oriented in different positions relative to the chamber 12. It will be noted, that at the position indicated by line A in FIG. 4, open areas 60, 66 of the first and second passages 54, 56 correspond with one another. Moving in a counter clockwise direction from line A—A, at line B—B, the constricted portion 64 of the first passage 54 corresponds to an open area 66 of the second passage 56. Again, moving counter clockwise from line B to the position indicated at line C—C, again the other open area 62 of the first passage 54 corresponds to the constricted area 68 of the second passage 56.

Referring to FIGS. 3 and 4, the clamp 14 may include indicia to indicate to the user what position the clamp is in, in relation to the chamber 12 for a particular flow condition. For example, the clamp 14 may include one and preferably a multiple of unique markings or indicia 70 which when aligned with a marker 72 designate to the user the position of the clamp.

In addition to facilitate manipulation of the clamp 14 and outer edge 80 may be configured with one or more indentations 82 or other means to facilitate the grasping and movement of the clamp.

The operation of an exemplary burette chamber 12 will now be described with respect to the use of the flow control clamp 14 to achieve various, desired flow modes of flow into and out of the chamber 12 through the tubes 20a and 20b and corresponding ports 38, 40. Specifically, the flow conditions and respective clamp 14 positions are: (1) filling or priming the chamber 12 from an associated solution source container, this is referred to as the prime position and corresponding to line A—A on FIG. 4; (2) administering a predetermined amount of solution to a patient from the chamber 12, this is referred to as the intermittent position and corresponding to B—B on FIG. 4; and (3) continuous flow of solution from the solution container through the chamber 12 and to the patient, which is referred to as the continuous flow position and corresponds to C—C.

To prime the chamber 12, the clamp 14 is pivoted such that the passage portions 60, 66 lying along line A—A (FIG. 4) are positioned in alignment with the inlet ports 38, 40. An indicia 70 labeled "prime" may be aligned with the marker 72 (FIG. 3) to indicate to the user that the clamp 14 is in the prime position. For purposes of the present description, the first passage 54, that is the passage closest to the hinge 53, has the fill tube 20a, which is connected to the source container (not shown), passing therethrough. The second tube passage 56, that is the outermost passage, has the tube 20b of the tube set 20 passing therethrough and tube 20b that is used to vent air from the chamber 12. The vent tube 20b may utilize a filter 73.

In the prime position, both the fill tube 20a and vent tube 20b (e.g., associated with ports 38, 40), are open. Solution flows from the source container (not shown) into the chamber 12, and further permits air to vent from the chamber 12 through the vent tube 20b. When a desired quantity of fluid flows into the chamber 12 the user pivots the clamp 14 to the position indicated at line B—B, the intermittent position, to stop the flow of fluid from the source container into the chamber 12. In this position, additional fluid is prevented from entering the chamber 12, and the patient can be administered with only the fluid in the chamber 12. An indicia 70 labeled "Interm" may be aligned with the marker 72 to indicate to the user that the clamp is in the intermittent position. When the lower clamp 18 is opened, air flowing through the vent tube 20b and port 40, permits the contents of the chamber 12 to flow freely from the chamber 12 to the patient without pulling a vacuum in the chamber 12. In this manner, a predetermined amount of solution only can be administered to the patient, without requiring continuous monitoring of a source container.

By pivoting the clamp 14 to the continuous flow position, in which the portions of the passages 54, 56 indicated at line C—C overlay the inlet ports 38, 40, a continuous flow of solution can be administered to the patient. An indicia 70 labeled "Contin" may be aligned with the marker 72 to indicate to the user that the clamp 14 is in the continuous position. In this position, fluid from the solution container flows into the chamber 12 through the open fill tube 20a. However, the air vent tube 20b is constricted or occluded, which prevents air from flowing out of the chamber 12 through the vent tube 20b and the flooding of the chamber 12. A lower tubing clamp 18 (FIG. 2) is typically used then to create a controlled solution flow profile from the drip chamber 12 to the patient.

The present flow control clamp 14 provides a number of advantages over known flow control clamp devices. First, as is readily apparent from the figures, the present clamp 14 is attached to the cap 28 of the chamber 12. Thus, it is no longer necessary to provide or locate, a separate flow control or clamp device.

In addition, it will be appreciated by those skilled in the art that the present device permits single-handed setting or positioning of the clamp to achieve such desired flow modes in one motion. That is, once the vent and supply tubes are positioned in the chamber cap 28, the clamp 14 can be pivoted between the prime, intermittent and continuous flow positions with one hand, merely by pivoting the clamp 14. Thus, a desired flow condition can be quickly and easily set with minimal effort, merely by pivoting the flow control clamp 14.

Also the clamp 14 occludes or opens the fill tube 20a and vent tube 20b in the necessary arrangement for the prime, intermittent and continuous modes thereby freeing up the user form having to remember the unique arrangement of individual tubing clamps found in prior art devices.

Also, there is little limit to the various arrangements of different slot configurations, number of slots and tubings to which the present invention may be applied. As can be seen altering these elements may provide for multiple flow modes which may be applied to other types of chambers and in other applications.

From the foregoing it will be observed that numerous modifications and variations can be effectuated without departing from the true spirit and scope of the novel concepts of the present invention. It is to be understood that no limitation with respect to the specific embodiment illustrated is intended or should be inferred. The disclosure is intended to cover by the appended claims all such modifications as fall within the scope of the claims.

For example, the clamp may be attached or operably attached to the container by being attached directly to the container or attached to an intermediate piece which is attached to the container or to one or more of a set of intermediate pieces, one or more of which are attached to the container.

What is claimed is:

1. A chamber for use with a fluid administration set, the chamber comprising a main body and a cap on the main body, the cap having an inlet port and a pivot member spaced from the inlet port, the chamber further including a clamp having a body portion pivotably mounted thereto about the pivot member, and forming an elongated tube receiving opening formed in the body portion spaced from the pivot member, the opening having at least one wide portion and at least one narrow portion, the body portion being operably attached to the pivot member with the opening overlying the cap inlet port.

2. The chamber in accordance with claim 1 wherein the cap includes two inlet ports and wherein the clamp having a second elongated tube receiving opening spaced from the first opening, the second opening being positioned in the body so as to overlay the second inlet port.

3. The chamber in accordance with claim 2 wherein the second opening includes an elongated large cross-sectional area connected to a narrow channel.

4. The chamber in accordance with claim 3 wherein the first opening has two wide portions connected by at least one narrow portion, wherein one wide portion and the at least one narrow portion are aligned with the second opening elongated large cross-sectional area relative to the pivot member and the second of the first opening wide portions is aligned with the second opening narrow channel.

5. The chamber in accordance with claim 1 wherein the opening includes a plurality of wide portions with a wide portion extending from each end of the narrow portion.

6. A chamber for use in a parenteral fluid administration set comprising:
a chamber body;
an end cap positioned on an end of the chamber body, the end cap having an inlet port therein and a first pivot element, the inlet port being spaced from the first pivot element; and
a flow adjusting tube clamp including a body portion having a second pivot element engageable with the first pivot element, the body portion including an elongated tube receiving opening formed therein, the opening being in spaced relation to the second pivot element so as to lie at a radial distance from the second pivot element, the opening having a generally dog-bone shape defining first and second spaced apart large areas contiguous with an occluding portion having a narrow cross-sectional area connecting the large areas, wherein the body portion is positioned on the cap with the first and second pivot elements engaging one another and with the opening overlying the cap inlet port.

7. The chamber in accordance with claim 6 wherein the cap includes two inlet ports and wherein the clamp includes a second elongated tube opening spaced from the first tube opening and positioned in the body so as to overlay the second inlet port.

8. The chamber in accordance with claim 7 wherein the second opening includes an elongated large area contiguous with an occluding portion.

9. The chamber in accordance with claim 8 wherein one of the first opening large areas and the occluding portion are aligned with the second opening large area relative to the pivot elements, and wherein the other of the first opening large areas is aligned with the second opening occluding portion relative to the pivot elements.

10. The chamber in accordance with claim 6 wherein the first and second large areas are substantially identical.

11. The chamber in accordance with claim 6 wherein the cap is generally circular and the first pivot element is eccentrically positioned thereon.

12. A chamber for use in a parenteral fluid administration set comprising:
a cylindrical chamber body;
a circular end cap positioned on an end of the chamber body, the end cap having two inlet ports therein and a first pivot element eccentrically positioned thereon, the inlet ports being spaced from one another and from the first pivot element; and
a flow adjusting tube clamp including a body portion having a second pivot element engageable with the first pivot element, the body portion including first and second elongated, arcuate tube receiving openings formed therein, the first and second openings being spaced from one another and from the second pivot element so as to lie at first and second radial distances from the second pivot element, the first opening having a dog-bone shape including substantially identical first and second large, open areas connected to one another by a narrow, channel-like occluding portion and the second opening including an elongated, large, open area contiguous with a narrow, channel-like occluding portion, wherein the body portion is positioned on the cap with the first and second pivot elements engaging one another and with the first and second openings overlying the cap inlet ports, and wherein one of the first opening large, open cross-sectional areas and the first opening occluding portion are aligned with the second opening large, open cross-sectional area relative to the pivot elements, and the other of the first opening large, open cross-sectional areas is aligned with the second opening occluding portion.

13. The chamber in accordance with claim 12 wherein the first pivot element includes an inlet port.

14. A parenteral fluid administration device comprising:
a chamber having a chamber body and an end cap positioned on an end of the chamber body, the end cap having an inlet port therein and a pivot element, the inlet port being in spaced relation to the pivot element, a flow adjusting tube clamp positioned on the cap pivotally mounted thereto at the pivot element, the clamp defining an elongated tube receiving opening being in spaced relation to the pivot element so as to lie at a radial distance from the pivot element, the opening defining first and second spaced apart large open cross-sectional areas contiguous with an occluding portion having a narrow, channel-like area connecting the large cross-sectional open areas, wherein the opening overlays the cap inlet port; and at least one tube in fluid communication with the chamber.

15. The parenteral fluid administration device in accordance with claim 14 wherein the end cap includes two inlet ports and wherein the clamp includes a second elongated tube opening spaced from the first tube opening and positioned in the body so as to overlay the second inlet port.

16. The parenteral fluid administration device in accordance with claim 15 wherein the second opening includes an elongated, large, open area contiguous with a narrow, channel-like occluding portion.

17. The parenteral fluid administration device in accordance with claim 16 wherein one of the first opening large areas and the occluding portion are aligned with the second opening large area relative to the pivot elements, and wherein the other of the first opening large areas is aligned with the second opening occluding portion relative to the pivot elements.

18. The parenteral fluid administration device in accordance with claim 14 wherein the chamber end cap is generally circular and the first pivot element is eccentrically positioned thereon.

19. The parenteral fluid administration device in accordance with claim 14 wherein the first and second large cross-sectional open areas are substantially identical.

20. The parenteral fluid administration device in accordance with claim 14 wherein the first pivot element includes an inlet port.

21. A device for use with an administration set comprising:

a container having a hollow body portion forming an internal chamber, a cap and a first tubing segment attached to the cap;

a clamp attached to the cap and movable relative to the cap, the clamp forming a first slot with the first tubing segment extending through the first slot, the first slot having at least a portion dimensioned to selectively pinch the first tubing segment in dependence on the position of the first tubing segment within the portion of the first slot.

22. The device of claim 21 wherein the cap is generally disk-shaped with the clamp generally wedge-shaped and attached to the cap generally at the apex of the clamp, the first slot being generally arcuate-shaped.

23. The device of claim 22 wherein the cap includes an injection site the clamp being pivotally attached to the site.

24. The device of claim 21 wherein the clamp is pivotally attached to the cap.

25. The device of claim 21 including a second tubing segment attached to the cap, the clamp forming a second slot with the second tubing segment extending through the second slot, the second slot having at least a portion dimensioned to selectively pinch the second tubing segment in dependence on the position of the second tubing segment within the portion of the second slot.

26. A device for use with an administration set comprising:

a container having a hollow body portion forming an internal chamber, a cap and a first tubing segment and a second tubing segment in fluid communication with the chamber;

a clamp attached to the container yet movable relative to the chamber, the clamp forming a first slot with the first tubing segment extending through the first slot, the first slot having at least a portion dimensioned to selectively pinch the first tubing segment in dependence on the position of the first tubing segment within the portion of the first slot and a second slot with the second tubing segment extending through the second slot, the second slot having at least a portion dimensioned to selectively pinch the second tubing segment in dependence on the position of the second tubing segment within the portion of the second slot.

* * * * *